(12) United States Patent
Obinata

(10) Patent No.: US 7,551,283 B2
(45) Date of Patent: Jun. 23, 2009

(54) ORIENTATION METER

(75) Inventor: Hirohiko Obinata, Tokyo (JP)

(73) Assignee: Yokogawa Electric Corporation, Tokyo (JP)

( * ) Notice: Subject to any disclaimer, the term of this patent is extended or adjusted under 35 U.S.C. 154(b) by 394 days.

(21) Appl. No.: 11/523,601

(22) Filed: Sep. 20, 2006

(65) Prior Publication Data

US 2007/0091313 A1    Apr. 26, 2007

(30) Foreign Application Priority Data

Sep. 20, 2005    (JP) ................... P.2005-271293

(51) Int. Cl.
   *G01N 21/84*    (2006.01)
(52) U.S. Cl. .................................... 356/429
(58) Field of Classification Search .............. None
   See application file for complete search history.

(56) References Cited

U.S. PATENT DOCUMENTS 5,313,260 A * 5/1994 Magyar et al. ............ 356/4.07
5,777,743 A * 7/1998 Bacchi et al. ............... 356/370

FOREIGN PATENT DOCUMENTS

| EP | 0 379 281 A3 | 7/1990 |
| JP | 11-269789 A | 10/1999 |
| JP | 11-269790 A | 10/1999 |
| WO | 99/67625 A1 | 12/1999 |
| WO | WO 01/75423 A1 | 10/2001 |
| WO | 2006/124315 A1 | 11/2006 |

* cited by examiner

*Primary Examiner*—Michael P Stafira
(74) *Attorney, Agent, or Firm*—Sughrue Mion, PLLC

(57) ABSTRACT

An orientation meter for measuring an orientation of a measuring object, the orientation meter including: a plurality of light emitting elements for irradiating light to the measuring object; a light receiving element for receiving reflected light being reflected by the measuring object; and a gain adjusting light emitting element arranged at a vicinity of the light receiving element, wherein the plurality of light emitting elements is arranged around the light receiving element, and the orientation of the measuring object is measured based on a signal from the light receiving element.

13 Claims, 10 Drawing Sheets

US 7,551,283 B2

ORIENTATION METER

This application claims foreign priority based on Japanese Patent application No. 2005-271293, filed Sep. 20, 2006, the content of which is incorporated herein by reference in its entirety.

BACKGROUND OF THE INVENTION

1. Field of the Invention

The present invention relates to an orientation meter for optically measuring in noncontact a fiber orientation or a molecular orientation of a film sheet or a paper, and relates to an orientation meter achieving high speed/high accuracy formation, small-sized formation, and low cost formation.

2. Description of the Related Art

An orientation meter is an apparatus for measuring, starting from a fiber orientation of paper, a molecular orientation represented by a plastic film sheet, an orientation property including a mixing degree of a fibrous filler and other filler which are mixed in a reinforced plastic, an orientation characteristic brought about by a rubbing processing of a liquid crystal fabricating procedure, or the like. As ways for measuring an orientation, there are adopted various measuring methods such as by a supersonic wave, a dielectric constant, a microwave, transmitted light, reflected light, a microscope.

The related arts with regard to a fiber orientation meter for optically measuring in noncontact a fiber orientation of paper are, for example, JP-A-11-269790 and a domestic republication of a PCT patent application No. WO01/075423.

FIG. 13A illustrates a sectional view, and FIG. 13B illustrates a bottom view of a fiber orientation meter described in JP-A-11-269790. In FIG. 13A, a light source 111 is LED, laser, or the like installed substantially vertically with respect to a measuring object 112, and light irradiated from the light source 111 is condensed to the measuring object 112 by using a condensing lens 113.

Light receiving elements 114 are light receiving diodes, 8 through 12 pieces of which are provided for example, with the light source 111 as its center, for receiving light reflected from the measuring object 112 and converting the reflected light into an electric signal. The light receiving elements 114 measure an orientation direction by selecting an angle of reflection θ with respect to, for example, an optical axis, to about 55 degrees.

A light receiving element holding portion 115 includes a flange portion 116 in a ring-like shape, light receiving element mounting holes 117 provided for the respective light receiving elements, and a lens mounting hole 118 for holding the condensing lens 113. A light source holding portion 119 is fixed to the light receiving element holding portion 115 concentrically with the lens mounting hole 118, and holds the light source 111 in a predetermined position.

FIG. 13B is the bottom view of the light receiving element holding portion 115. Here, a positioning portion 120 is formed by notching a portion of the flange portion 116 to uniquely determine an angle of attaching the light receiving element holding portion 115 to a casing (not illustrated). Here, twelve light receiving element mounting holes 117 are provided, and light receiving element fixing holes 122 are provided in one to one relationship with the light receiving element mounting holes 117. An upper outer peripheral portion 123 is a cylindrical portion provided concentrically with the lens mounting hole 118 and is fixed with the light source holding portion 119.

In the above-described configuration, a distribution of reflected light, the light being reflected by the measuring object 112, is measured by irradiating light from the light source 111 to the measuring object 112, and using the light receiving elements 114 arranged at a side face of the light receiving element holding portion 115 with respect to an axis of light irradiated from the light source 111.

FIG. 14 shows a flow of a signal, a signal converted into an electric signal by the light receiving element 114 is inputted to an A/D converter 131 as an element signal 130. After measuring a distribution of light by a distribution measuring section 132, a measured value 134 is outputted by calculating an orientation direction by an orientation calculating section 133.

Meanwhile, according to an orientation meter having such a configuration, a number of the light receiving elements 114 are needed for maintaining a measurement accuracy and therefore, it is necessary to prepare the A/D converters 131 as many as the number of the light receiving elements.

In this case, cost of the A/D converter 131 is high, and also a component volume is increased and therefore, a problem that it is difficult to downsize the orientation meter is posed.

Further, separately from the orientation meter, when light is made to be incident on the measuring object from a vertical direction, and reflected light is detected by a plurality of light receiving elements arranged on a reflection side, there poses a problem that a guided light component becomes smaller than a surface reflected component of the measuring object and it is difficult to acquire orientation information, and particularly, in a thin film, since a transmitted light component becomes large, a component of guided light leaked in a direction of a reflecting face is reduced and therefore, it is difficult to acquire orientation information.

Further, although an orientation is investigated by utilizing a propagating speed by a dielectric constant or a supersonic wave, or a microwave, there poses a problem that the method is not suitable for online high speed measurement, further, it is difficult to ensure accuracy.

SUMMARY OF THE INVENTION

The present invention has been made in view of the above circumstances, and provides an orientation meter capable of:
1) promptly measuring an orientation characteristic of a measuring object represented by a fiber orientation of a measuring object, a molecular orientation of a film, an orientation of a filler in plastic and an orientation by a rubbing processing or the like;
2) reducing cost of a component including an A/D converter; and
3) downsizing by reducing a component volume.

In some implementations, an orientation meter of the invention for measuring an orientation of a measuring object, comprising:
a plurality of light emitting elements for irradiating light to the measuring object;
a light receiving element for receiving reflected light being reflected by the measuring object; and
a gain adjusting light emitting element arranged at a vicinity of the light receiving element,
wherein the plurality of light emitting elements is arranged around the light receiving element, and
the orientation of the measuring object is measured based on a signal from the light receiving element.

In some implementations, an orientation meter of the invention for measuring an orientation of a measuring object, comprising:
a plurality of light emitting elements for irradiating light to the measuring object;

a light receiving element for receiving reflected light being reflected by the measuring object; and a reflector or a light guide for directing the light from the plurality of light emitting elements to a surface of the measuring object and a region in the vicinity of directly below the light receiving element, wherein the orientation of the measuring object is measured based on a signal from the light receiving element.

In some implementations, an orientation meter of the invention for measuring an orientation of a measuring object, comprising:

a plurality of light emitting elements for irradiating light to the measuring object;

a light receiving element for receiving reflected light being reflected by the measuring object; and a non-oriented reflector arranged at a position that is opposed to the light receiving element, the position being on a back face side of the measuring object, wherein the orientation of the measuring object is measured based on a signal from the light receiving element.

In the orientation meter, the plurality of light emitting elements are arranged along a circumference at equal intervals by a predetermined angle with respect to a surface of the measuring object, and the light receiving element is arranged at the vicinity of a center of the light emitting elements.

In some implementations, an orientation meter of the invention for measuring an orientation of a measuring object, comprising:

a plurality of light emitting elements for irradiating light to the measuring object; and at least one light receiving element arranged with the measuring object being interposed between the light emitting elements and the light receiving element, wherein the light irradiated from the plurality of light emitting elements is transmitted through the measuring object, and the orientation of the measuring object is measured based on a signal from the light receiving element, the signal made by receiving the transmitted light.

In some implementations, an orientation meter of the invention for measuring an orientation of a measuring object, comprising:

a plurality of light emitting elements for irradiating light to the measuring object; and a plurality of light receiving elements arranged with the measuring object being interposed between the light emitting elements and the light receiving elements, each of the plurality of light receiving elements and each of the plurality of light emitting elements making a pair, wherein the light irradiated from the plurality of light emitting elements is transmitted through the measuring object, and the orientation of the measuring object is measured based on signals from the plurality of light receiving elements, the signals made by receiving the transmitted light.

The orientation meter further comprising:

a storage for storing individual differences of the respective light emitting elements, wherein in calculating an orientation direction of the measuring object, calibration is executed based on the individual differences stored in the storage.

In the orientation meter, the signal from the light receiving element is loaded by using a reference position signal and a timing signal for making the plurality of light emitting elements sequentially emit light, or by using the reference position signal and a signal from a circuit that catches the sequentially emitted light as a timing signal.

In the orientation meter, an order of emitting light of the plurality of light emitting elements makes a substantially uniform distribution.

In the orientation meter, the light from the light emitting element for irradiating the measuring object is a P polarized light or a S polarized light.

In the orientation meter, the light receiving element is a semiconductor photodetector, and the light emitting element is a light emitting diode (LED) or a laser diode.

In the orientation meter, at least one timing signal for making the plurality of light emitting elements sequentially emit light or at least one signal from a circuit that catches the sequentially emitted light as a timing signal is used as a reference position signal by changing a duty of at least one timing signal or at least one signal from the circuit with other signal, and the signal from the light receiving element is loaded by using the reference position signal.

In the orientation meter, a frequency of the light emitted from the respective light emitting elements is changed in accordance with a characteristic of the measuring object.

In the orientation meter, a number of the plurality of light emitting elements is even, the plurality of light emitting elements is arranged along a circumference, and two of the light emitting elements that are opposed to each other emit light simultaneously.

The orientation meter further comprising:

a software for calculating an orientation direction of the measuring object having a fiber orientation and an orientation direction of the measuring object having a molecular orientation, wherein the software is switched to calculate the orientation direction of the measuring object having the fiber orientation or the orientation direction of the measuring object having the molecular orientation in accordance with a usage.

DESCRIPTION OF THE PREFERRED EMBODIMENTS

Figure 1:
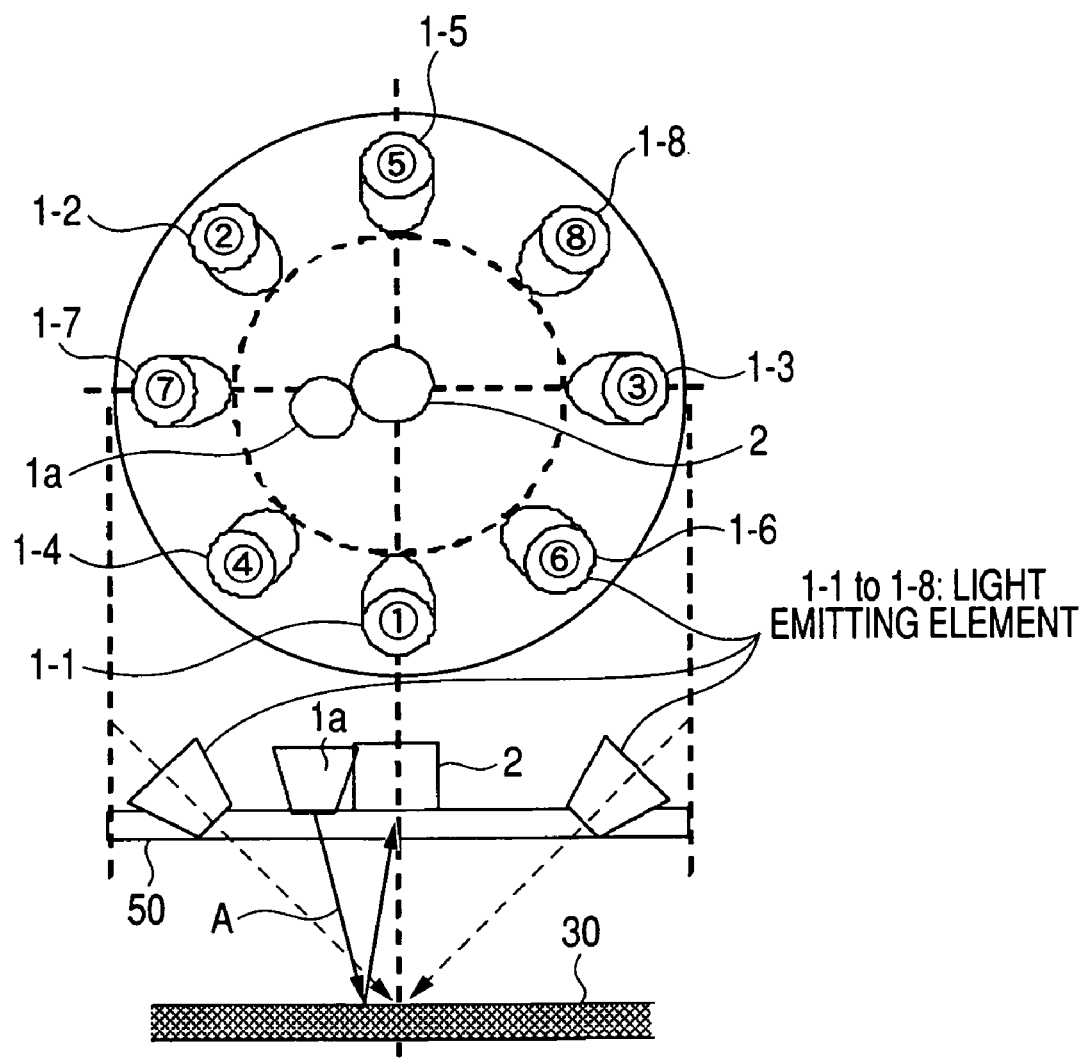
FIG. 1 is a configuration view showing an embodiment of an orientation meter according to an embodiment of the invention.

The invention will be explained in details in reference to drawings as follows. FIG. 1 is a configuration view showing an orientation meter according to an embodiment of the invention.

In FIG. 1, reference numerals 1-1 through 1-8 denote light emitting elements of LED, laser or the like, and reference numeral 50 denotes a light emitting element holding member in a shape of a circular plate. Reference numeral 2 denotes a light receiving element including a light receiving diode or the like, and the light emitting elements 1-1 through 1-8 are attached at a vicinity of a peripheral edge of the light emitting element holding member 50 in the shape of the circular plate at equal intervals. The light emitting elements are arranged at a predetermined angle with respect to a measuring object such that the lights emitted thereby irradiate substantially the same location of the measuring object 30. A portion of scattered light that is reflected by the measuring object 30 is received by the light receiving element 2 arranged at a vicinity of a center of the light emitting element holding member 50.

A gain adjusting light emitting element 1a is a light emitting element arranged at a vicinity of the light receiving element, separately from the light emitting elements 1-1 through 1-8 arranged in directions oblique to the measuring object 30, and light A emitted from the gain adjusting light emitting element 1a is reflected by substantially vertical face of the measuring object 30. By referring to light reflected by substantially the vertical face, the gain of the light emitting element can be adjusted. For example, by adjusting the gain such that reflected light from the gain adjusting light emitting element 1a becomes constant, and applying the similar gain to the respective light emitting elements arranged along a side face, a variation in S/N by a material or a variation in distance of a sheet face can be restrained.

Figure 2:
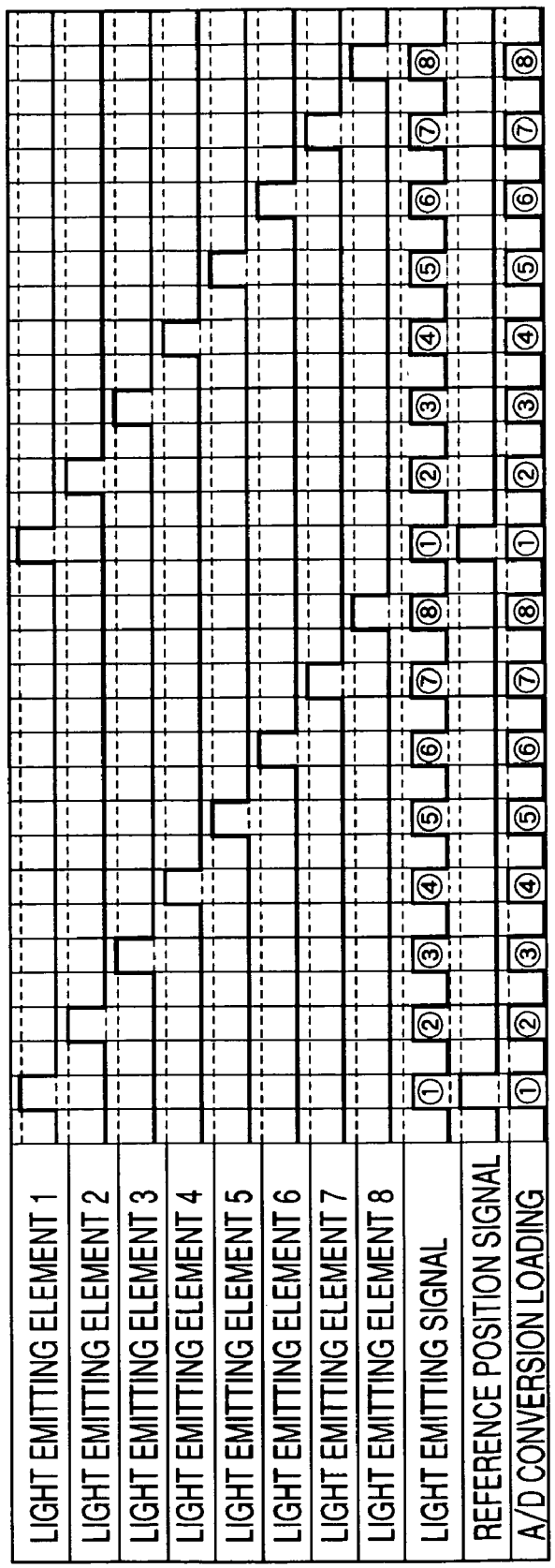
FIG. 2 is an explanatory diagram showing a reference position signal and a light emitting signal at a loading timing of an A/D converter.

The light emitting element 1-1 through 1-8 emit light by timings as shown by, for example, FIG. 2 to irradiate the measuring object 30, and the light receiving element 2 measures reflected light from the measuring object 30 in accordance with the light emitting timings of the respective light emitting elements, and stores the measurement result. In FIG. 2, a reference position signal is generated along with the light emitting element 1-1, the light emitting elements 1-2 through 1-8 sequentially emit light by the predetermined timings, a light emitting signal is photoelectrically converted by the light receiving element, and an A/D converter (not illustrated) loads an electric signal. Further, as a light emitting order, light is emitted so as to make a substantially uniform distribution at the side face.

Although an order of emitting light of the light emitting elements arranged uniformly on a circumference may be a sequential light emission in the clockwise direction or the counter clockwise direction, when light is emitted so as to make a uniform distribution in the light emitting order, since a measuring face changes over time in online measurement, the sequential light emission is effective.

That is, when the light emitting element arranged at a position of 1-1 emit light first as shown in FIG. 1, next, the light emitting element at a position of 1-2 shifted by 45 degrees, in the counter clockwise direction in view from above, from 1-5 arranged to be opposed thereto is made to emit light.

Next, the light emitting element at a position of 1-3 shifted by 45 degrees, in view from above in the counter clockwise direction, from 1-6 arranged to be opposed to the position of the light emitting element 1-2 is made to emit light. Similarly, the light emitting element at a position of 1-4 shifted by 45 degrees, in the counterclockwise direction in view from above, from 1-7 arranged to be opposed to the position of 1-3 is made to emit light and the operation is carried out until 1-8 to return to the start.

Further, although in the embodiment, the element shifted therefrom by 45 degrees in the counterclockwise direction is made to emit light, a similar effect is achieved by making the element shifted therefrom in the clockwise direction in view from above emit light. Further, even when a number of the light emitting elements is increased, the light emitting elements arranged along the circumference may emit light sequentially at positions as remote as possible from each other.

Further, as light irradiated from the light emitting element, P polarized light or S polarized light may be used in accordance with a characteristic of an absorbance of the measuring object. For example, since an absorbance of S polarized light is large at a reflecting face, there is a case in which S polarized light is useful for increasing S/N. As a method of forming P polarized light or S polarized light, a deflection plate may be added to a light emitting element, or a coherent light source of laser or the like may be used.

Figure 3:
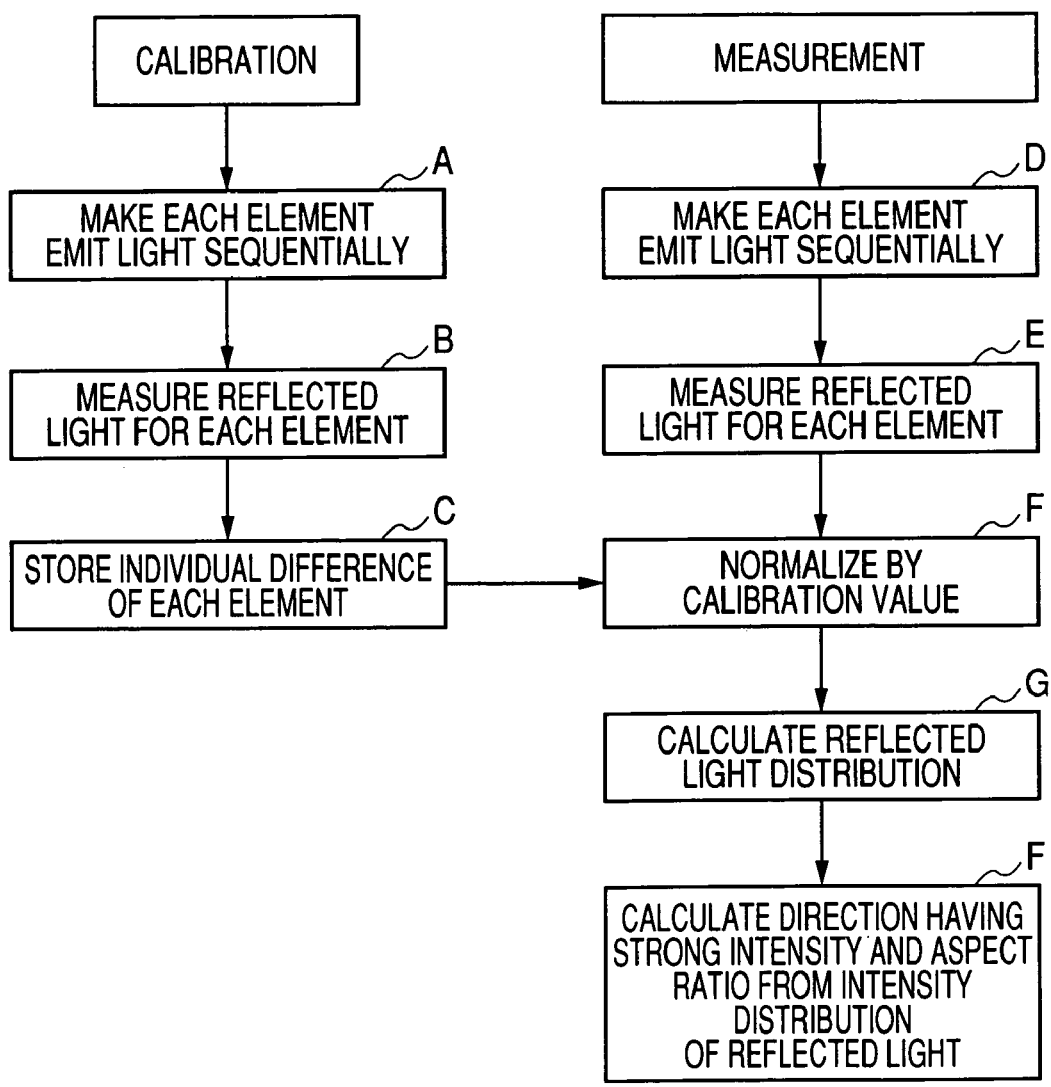
FIG. 3 is an explanatory diagram showing a flow of a measurement of the orientation meter according to an embodiment of the invention.

FIG. 3 shows a flow of a measurement of the orientation meter according to an embodiment of the invention, here, an individual difference is measured previously for each light emitting element, and the individual difference is stored to a storage. In measurement for removing the individual difference, a non-oriented reference face is prepared for the reflecting face.

In FIG. 3, in calibration, in (A), the respective light emitting elements are sequentially made to emit light, in (B), reflected light for each element is measured, in (C), the individual difference for each element is stored.

In the measurement, in (D), the respective light emitting elements are sequentially made to emit light, in (E), reflected light for each element is measured, in (F), the measured value is normalized by a calibration value stored to the storage.

Next, in (G), a reflection distribution is calculated, in (H), a direction having a strong intensity, and an aspect ratio are calculated from an intensity distribution of the reflected light.

That is, based on the normalized measured value, an elliptical approximation shown by the following equations is carried out, and a direction of an intensity distribution and the aspect ratio of the reflected light are calculated.

$$\theta = \frac{1}{2}a\tan\left(-\frac{Y}{X}\right) + \frac{m}{2}\pi \quad \ldots \text{ orientation angle}$$

$$T = \frac{a}{b} \ldots$$

orientation index (a: long diameter, b: short diameter)

$$X = \Sigma \frac{1}{r_n^2} \cos 2d_n$$

$$Y = \Sigma \frac{1}{r_n^2} \sin 2d_n$$

m=0 or ±1 (when |θ|<45°, m=0)
$d_n$: arrangement angle of light emitting element
$r_n$: normalized signal output of reflected light corresponding to each light emitting element
n: No. corresponding to each arrangement of light emitting element Further, although the intensity and the angle of orientation are calculated from the intensity distribution of the reflected light, as a method thereof, an approximation by a trigonometric function or other method may be used other than the above-described elliptical approximation.

In a case of a molecular orientation of a film or a filler in a plastic, a direction having a strong intensity of reflected light is obtained as an orientation direction of molecule or filler, in a case of fiber orientation of paper, a direction having a weak intensity of reflected light is obtained as an orientation direction of a fiber.

It seems that a phenomenon of the preceding paragraph is derived from the fact that in a case of a molecular orientation or a polymeric filler, by guiding light in an orientation direction of a molecule by an effect of Optical Wave Guide, light leaking out with respect to a reflecting face (here, simply referred to as reflected light) is intensified, and in a case of a fiber, reflected light is easily scattered in a direction of a cross-sectional face of the fiber and therefore, a reflection intensity is intensified in the direction, total reflection is easily brought about in a longitudinal direction and therefore, the reflection intensity is reduced in the direction.

Figure 4:
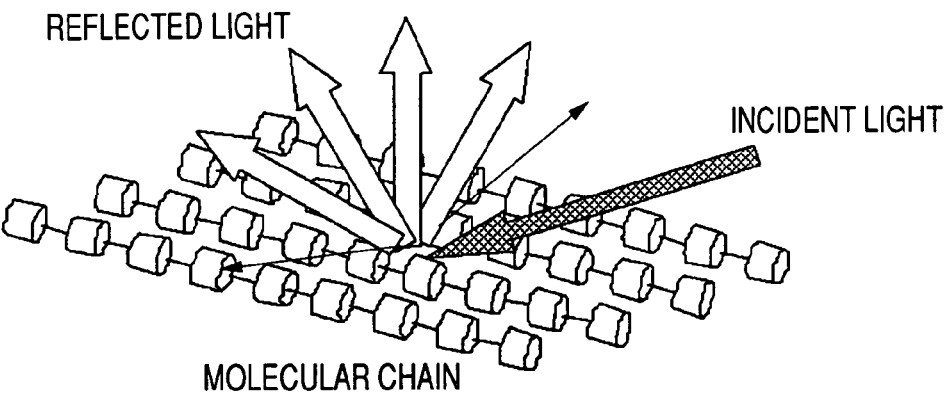
FIG. 4 is a view showing a concept of reflected light by a molecular orientation or a filler.
Figure 5:
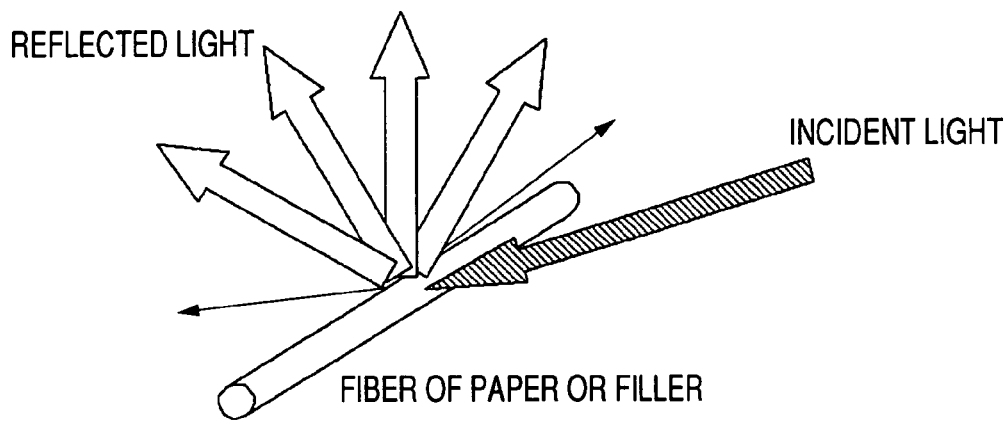
FIG. 5 is a view showing a concept of reflected light by fiber orientation.

FIG. 4 shows a concept of reflected light by a molecular orientation or a polymeric filler, FIG. 5 shows a concept of reflected light by a fiber orientation.

Figure 6:
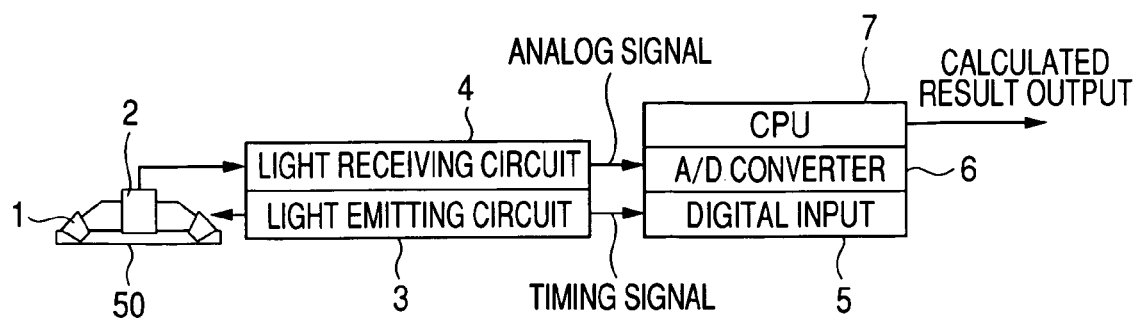
FIG. 6 is an explanatory diagram showing a configuration of a system of measuring an orientation direction according to an embodiment of the invention.

FIG. 6 shows an example of a configuration of a measurement system of the orientation meter according to an embodiment of the invention. The light emitting elements 1-1 through 1-8 sequentially repeat light emittance of, for example, 250 ns of the respective elements via a light emitting circuit 3. Reflected light at this occasion is caught by a light receiving circuit 4 via the light receiving element 2, and is loaded to an A/D converter 6 as an analog signal.

For example, when A/D conversion is carried out by 500 ns/1-point by using the A/D converter 6, in a case where a number of elements is 8, signals of the respective elements required for orientation calculation can be obtained by 4 ms.

A value subjected to A/D conversion is stored as data of each element position based on a timing signal from the light emitting circuit 3.

An output of the light emitting element may be controlled by a board having the light emitting circuit or maybe controlled on a side of CPU. An output timing of the light emitting element is not needed to be limited to 2 points of I/O, but 1 point maybe sequentially outputted to I/O, or outputs may individually be inputted to a number of I/O channels allocated with the respective elements. Therefore, a digital input 5 shown in FIG. 6 may be of a type of transmitting a timing signal to a side of the light emitting circuit with a side of CPU as a digital output.

Further, when 2 points of digital signals of a signal for a light emitting timing and a reference position signal are put together as one digital signal by changing duty (time rate of ON/OFF) of the signal, digital signal lines can be reduced from 2 to 1.

Further, when a light emitting control is on the side of CPU and the analog signal is inputted in synchronism therewith, the digital timing signal is unnecessary.

Further, by being used along with the reference position signal, the analog signal from the light receiving element 2 can continue to take positional correspondence accurately even when the measurement is repeated.

When a series of the respective element signals have been prepared, a distribution of reflected light is calculated by CPU 7 to output orientation angle/orientation index to a necessary apparatus by a method of digital data, analog data, a screen output or the like.

When at CPU, storing of data of the respective elements converted by A/D conversion is carried out by a high speed processing of about 200 ns by using a resident task having a high interruption priority or the like, and calculation of the orientation is processed in 2-4 ms by a main routine, there can be realized a highly accurate measurement capable of carrying out the high speed measurement with a small influence of a change in the position by a scanning of a sensor head or a flow of the measuring object 30.

Although the orientation of the film is conventionally frequently measured by off line, the orientation can also be measured by online when the orientation meter of an embodiment of the invention is used. Thereby, the invention can serve in an improvement in a number of steps required for fabricating a measuring object or yield thereof.

By constituting the single A/D conversion circuit and restraining a number of points of I/O, a product excellent in cost performance can be fabricated. This is effective in any of a film, a sheet, paper, an oriented film sheet or the like as the measuring object. Further, when a face of the measuring object constituting object of the measurement is substantially a plane, the measurement can be carried out even in a face having a characteristic of a spherical face, a wavy face or the like in a final or a middle procedure thereof to achieve an effect similar to the above-described.

According to a liquid crystal film, a molecular orientation directly affects a property thereof and therefore, it is necessary to measure an orientation thereof and the invention can also be used in measuring the orientation.

Further, in a reaction of inserting lithium to a carbon negative electrode which is frequently used for a battery electrode material in recent years, it seems to be effective for improving a negative electrode characteristic to make clear an orientation property of an inert film or a highly oriented thermally decomposed graphite or the like. The invention can also be used for measuring the orientation property.

Further, also in a multilayered film fabricated by utilizing a molecular beam, an investigation on a property of an orientation of a molecule produced at a board face amounts to an investigation on a property of a thin film per se. The invention can also be used for measuring the orientation property.

Further, there is a case of mixing various fillers such as a fibrous material into a plastic so as to increase a strength of the plastic. At this occasion, a degree and a direction of entwining, and a degree of mixing of the filler of the fibrous material effects a significant influence on a strength property. The degree and direction of entwining and the degree of mixing can be measured as an orientation, and the invention can also be used for measuring this kind of characteristic value.

Further, when a frequency of light emitted from the light emitting element is changed in accordance with the property of the measuring object, the highly accurate measurement in accordance with the property of the measuring object can be carried out.

Further, the light receiving element arranged substantially on the center of the light emitting elements is not limited to a single but two or more thereof may be provided, and the receiving signal may be increased, or the light receiving element may be selected in accordance with a transmitting frequency or a property of a light receiving face.

Figure 7A:
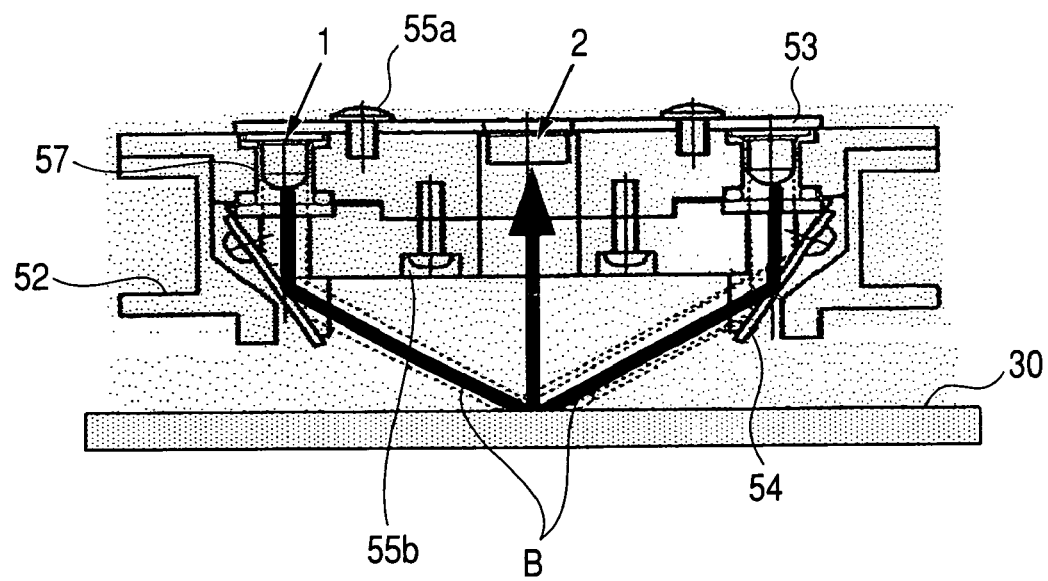
FIG. 7A illustrates a sectional view of an orientation meter according to other embodiment of the invention.
Figure 7B:
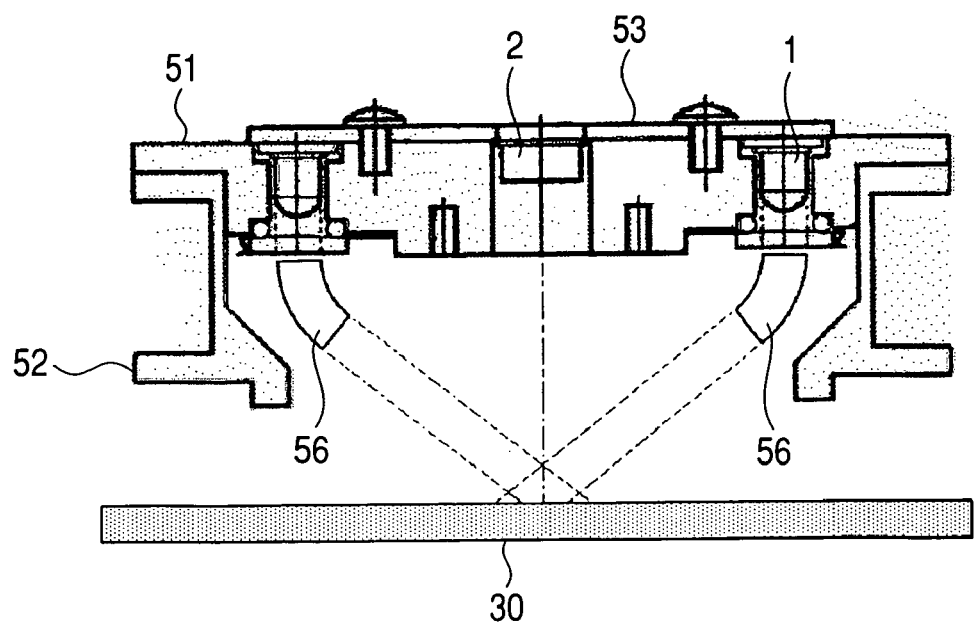
FIG. 7B illustrates a sectional view of an orientation meter according to other embodiment of the invention.

FIGS. 7A, 7B are sectional views showing other embodiments with regard to a method of attaching a light emitting element. In the embodiments, the light emitting element is fixed in a direction orthogonal to the measuring object 30. That is, in FIG. 7A, a plurality of the light emitting elements 1 are inserted into light emitting element fixing holes 57 along a circumference formed orthogonally to a surface of a first support member 51, held by a board 53 and is fixed by a screw 55a. According to the embodiment, the plurality of light emitting elements 1 irradiate light in directions orthogonal to the measuring object 30.

A second support member 52 fixed by a screw 55b to be opposed to the first support member 51 is arranged with a reflecting plate 54 a surface of which is formed by a shape of a recess face, circularly in a strip-like shape, light emitted from the plurality of light emitting elements 1 is reflected by the reflecting plate 54 to advance in B direction and scattered light reflected by the measuring object 30 is made to be incident on the light receiving element 2.

In FIG. 7B, there are provided light guide tubes 56 for guiding light emitted from the plurality of light emitting elements 1 in place of the reflecting plate 54 in the shape of the recess face.

According to the above-described configuration, fabrication thereof is facilitated since it is not necessary to form the hole of attaching the light emitting element by making an angle in an oblique direction.

Figure 8:
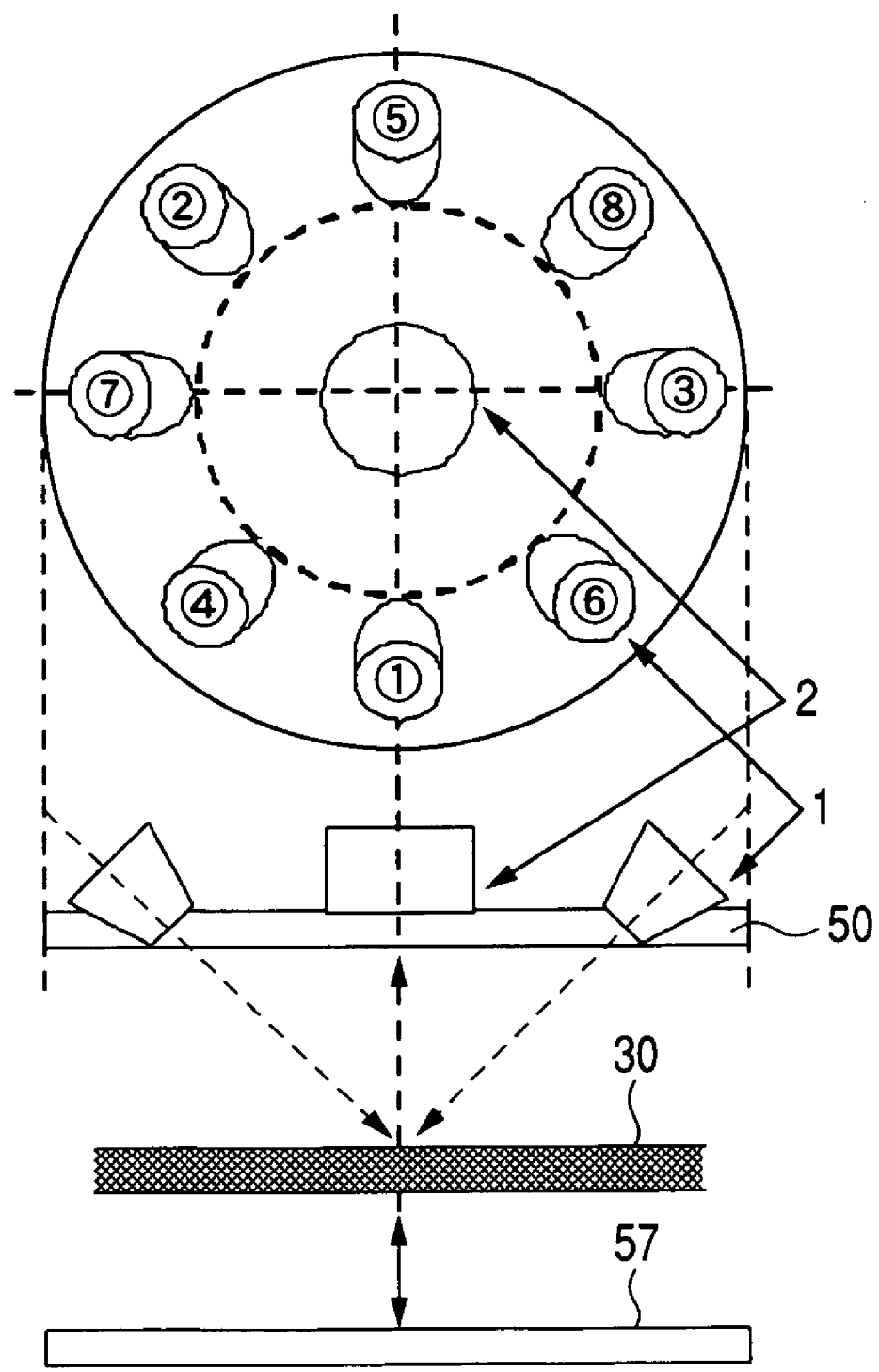
FIG. 8 is a configuration view of an orientation meter according to other embodiment of the invention.

In FIG. 8, a non-oriented reflecting plate 57 is arranged on a back side of the measuring object 30 right below the light receiving element 2. According to the configuration, an S/N ratio can be increased, that is, by reflecting light transmitted through the measuring object 30 to transmit through the measuring object 30 again, measuring components are increased by transmittance by a plurality of times, and due to a system having a closed opposed face, an effect of reducing noise by a stray light component can be achieved.

Figure 9:
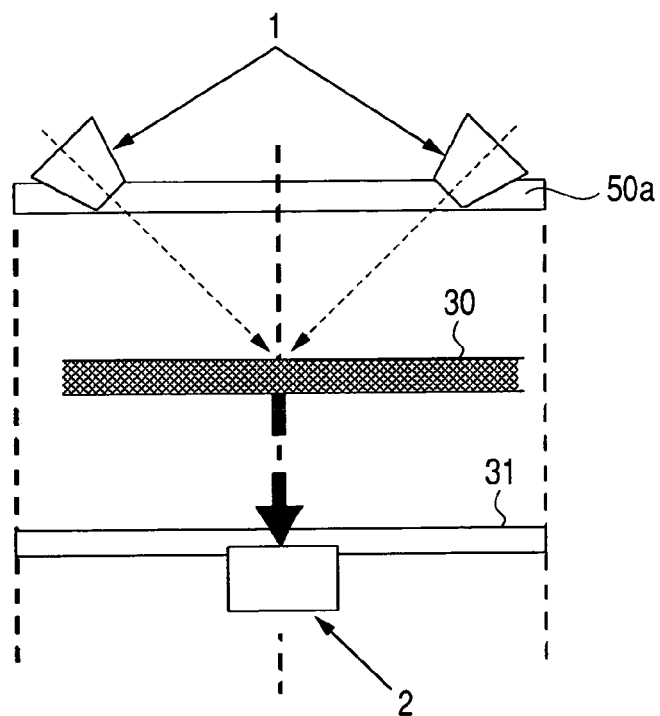
FIG. 9 is a configuration view of an orientation meter according to other embodiment of the invention.

In FIG. 9, the light receiving element 2 is arranged on the back side of the measuring object 30 and the light receiving element 2 measures an orientation of a fiber or a molecule based on light transmitted through the measuring object 30. Further, 8 through 12 pieces of the light emitting elements are arranged on the circumference as shown by FIG. 1 as a number thereof.

Figure 10:
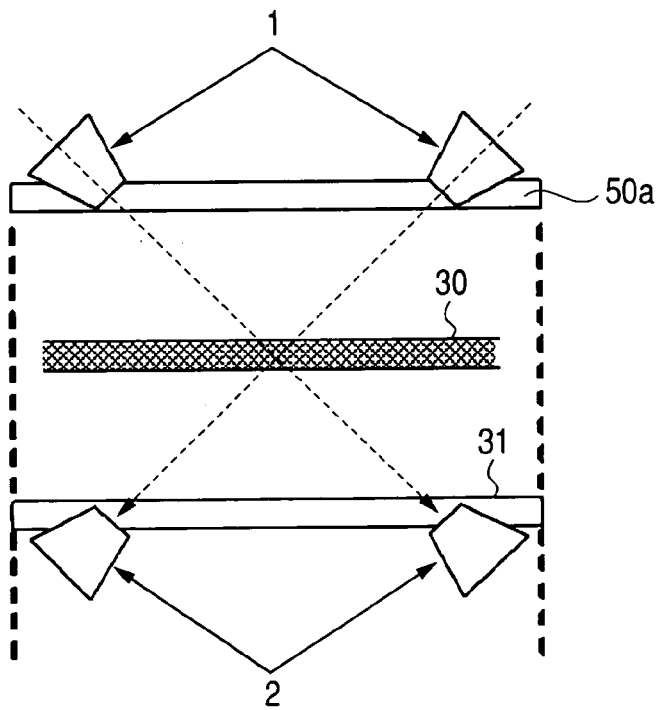
FIG. 10 is a configuration view of an orientation meter according to other embodiment of the invention.

In FIG. 10, the light receiving elements are arranged on the back side of the measuring object 30 to be respectively opposed to the light emitting elements, and an orientation of a fiber or a molecule is measured based on light transmitted through the measuring object 30. According to the example, the light emitting element 1 is held by a light emitting element holding member 50a and the light receiving element is held by a light receiving element holding plate 31. Further, a flow of measurement of the orientation meter and a circuit of calculating the orientation are similar to those shown in FIG. 3 and FIG. 6. Also in the case of the embodiment, 8 through 12 pieces of the light emitting elements are arranged along the circumference as shown by FIG. 1 as a number thereof and the same number of the light receiving elements are arranged to be opposed thereto.

Figure 11A:
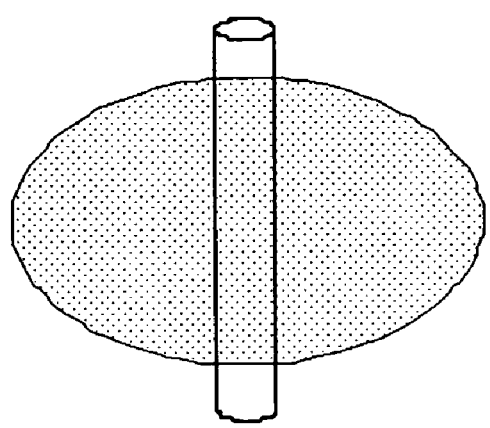
FIG. 11A illustrates an explanatory view showing an intensity distribution when a measuring object has a fiber orientation.
Figure 11B:
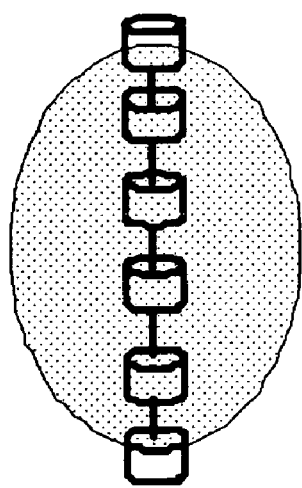
FIG. 11B illustrates an explanatory view showing an intensity distribution when a measuring object has a molecular orientation.

FIGS. 11A and 11B show a difference between a distribution of intensity of reflected light in a case in which the measured an object 30 is constituted by a fiber orientation (FIG. 11A) and a distribution of an intensity of guided light in a case of a molecular orientation represented by a plastic film sheet (FIG. 11B). As shown by the drawings, directions of the intensity distributions differ from each other by 90 degrees. Therefore, the orientation meter of an embodiment of the invention is provided with a software switch for converting a display (output) of the orientation direction by 90 degrees. Thereby, there can be used the same component for two uses of measurement of the molecular orientation of the film and measurement of the fiber orientation of paper.

Figure 12:
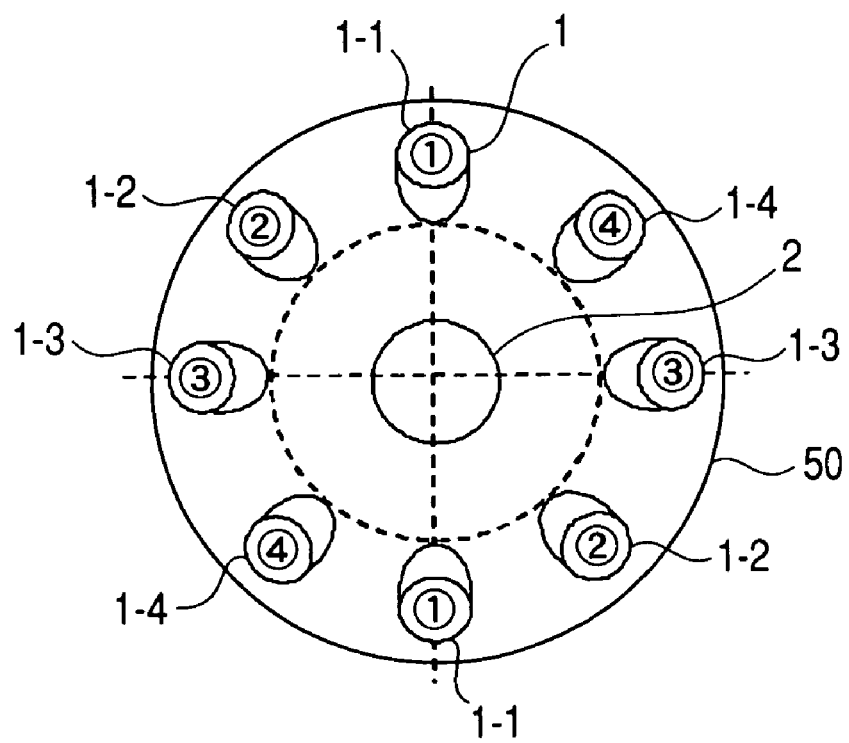
FIG. 12 is a configuration view of an orientation meter according to other embodiment of the invention.
Figure 13A:
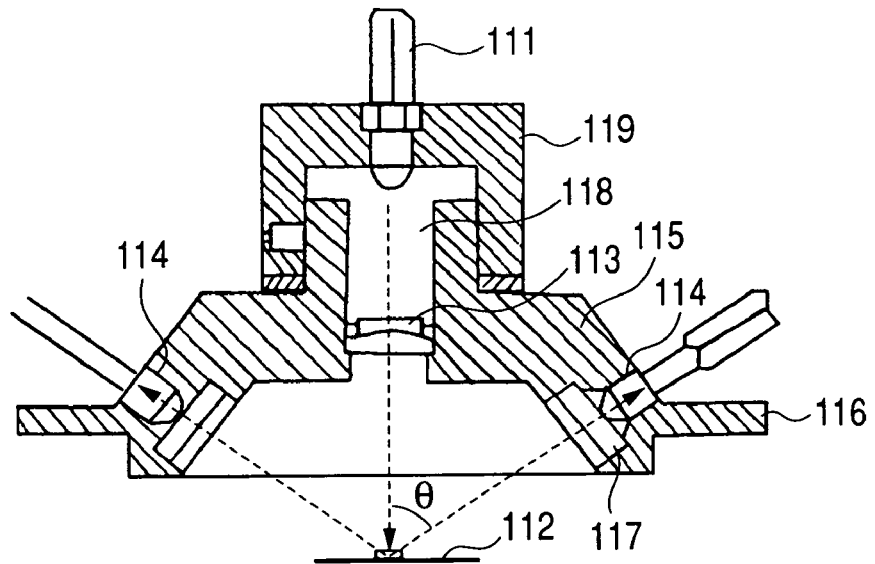
FIG. 13A illustrates a sectional view of a fiber orientation meter of a related art.
Figure 13B:
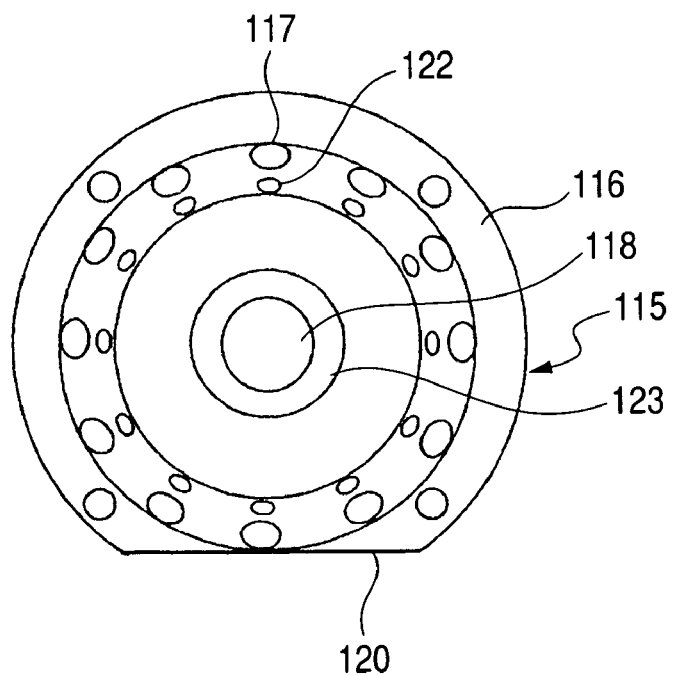
FIG. 13B illustrates a bottom view of the fiber orientation meter of a related art.
Figure 14:
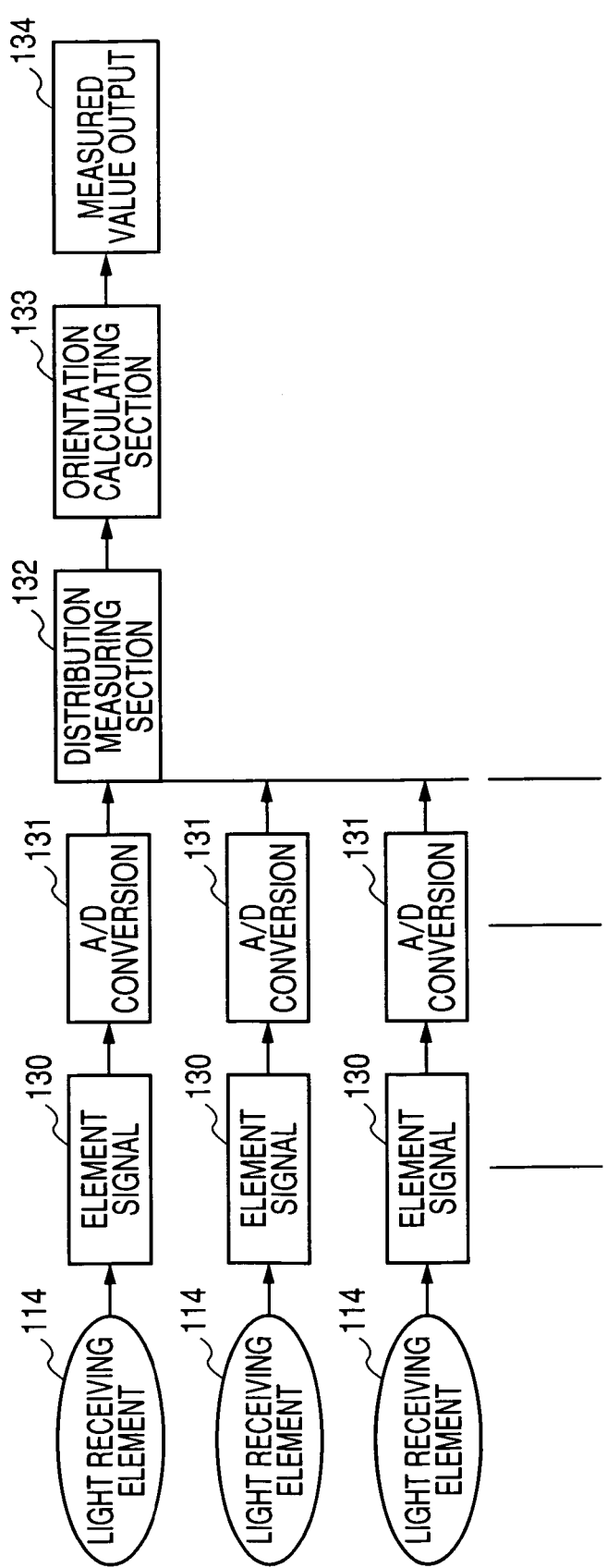
FIG. 14 is an explanatory diagram showing a flow of a signal of the fiber orientation meter of the related art.

In FIG. 12, when making even number of light emitting elements arranged on a circumference at intervals of uniform distances emit light, the light emitting elements opposed to each other are made to emit light simultaneously. By simultaneously irradiating light from two directions constituting a symmetry by an axis thereof as in an order of numbers of 1 though 4 as shown by the drawing, the S/N can be increased. Further, by simultaneously irradiating light from the two directions constituting the symmetry by the axis in this order, a twice number of elements can be arranged for one output signal and therefore, the arrangement serves to constitute the high resolution in detecting the signal. The arrangement is effective not only for increasing the resolution but also for increasing a sweep speed when an equivalent number of the light emitting elements is equivalent. Further, even when the surface of the measuring object is wavy, an averaged output can be achieved.

Further, the above-described explanation only shows a specific preferable embodiment with an object of explanation and exemplification of the invention. For example, a number of the light emitting elements or the like is not limited to that in the embodiment but can pertinently be changed.

For example, it is not necessarily needed that the duty of the light emitting signal shown in FIG. 2 is 50% but a light nonemitting time period may pertinently be reduced.

Directions of directing the light emitting element and the light receiving element may not strictly coincide with each other. Depending on a property of guiding light of a sample, there may be provided a distance to a degree of guiding light between a center position of light irradiated for increasing a guiding path and the center position of directing a light receiving element. Therefore, the invention is not limited to the above-described embodiment but includes a number of changes or modifications within the range not deviated from an essence thereof.

According to the invention, the following effect is achieved. In some implementations, an orientation meter of the invention for measuring an orientation of a measuring object, including:

a plurality of light emitting elements for irradiating light to the measuring object;

a light receiving element for receiving reflected light being reflected by the measuring object; and a gain adjusting light emitting element arranged at a vicinity of the light receiving element, wherein the plurality of light emitting elements is arranged around the light receiving element, and the orientation of the measuring object is measured based on a signal from the light receiving element.

Accordingly, a fiber orientation of a paper or a molecular orientation of a film, a filler orientation in a plastic can promptly be measured, a reduction in component cost and downsizing can be achieved since a single A/D converter is enough. Further, gains of the plurality of light emitting elements arranged along a circumference can be adjusted by using the gain adjusting light emitting element.

In some implementations, an orientation meter of the invention for measuring an orientation of a measuring object, including:

a plurality of light emitting elements for irradiating light to the measuring object;

a light receiving element for receiving reflected light being reflected by the measuring object; and a reflector or a light guide for directing the light from the plurality of light emitting elements to a surface of the measuring object and a region in the vicinity of directly below the light receiving element, wherein the orientation of the measuring object is measured based on a signal from the light receiving element.

Accordingly, manufacturing is facilitated since it is not necessary to form a hole for attaching the light emitting element with some angle in an oblique direction.

In some implementations, an orientation meter of the invention for measuring an orientation of a measuring object, including:

a plurality of light emitting elements for irradiating light to the measuring object;

a light receiving element for receiving reflected light being reflected by the measuring object; and a non-oriented reflector arranged at a position that is opposed to the light receiving element, the position being on a back face side of the measuring object, wherein the orientation of the measuring object is measured based on a signal from the light receiving element.

Accordingly, the light transmitted through the measuring object is reflected by the non-oriented reflector to transmit through the measuring object again. As a result, there can be achieved an effect of increasing a measuring component by twice transmission and a reduction in noise by a stray light component.

In the orientation meter, the plurality of light emitting elements are arranged along a circumference at equal intervals by a predetermined angle with respect to a surface of the measuring object, and the light receiving element is arranged at the vicinity of a center of the light emitting elements.

Accordingly, the orientation can accurately be measured.

In some implementations, an orientation meter of the invention for measuring an orientation of a measuring object, including:

a plurality of light emitting elements for irradiating light to the measuring object; and at least one light receiving element arranged with the measuring object being interposed between the light emitting elements and the light receiving element, or a plurality of light receiving elements arranged with the measuring object being interposed between the light emitting elements and the light receiving elements, each of the plurality of light receiving elements and each of the plurality of light emitting elements making a pair, wherein the light irradiated from the plurality of light emitting elements is transmitted through the measuring object, and the orientation of the measuring object is measured based on a signal from the light receiving element, the signal made by receiving the transmitted light.

Accordingly, the orientation of layers entirely in a thickness direction of the measuring object can further excellently be measured.

The orientation meter further including:

a storage for storing individual differences of the respective light emitting elements, wherein in calculating an orientation direction of the measuring object, calibration is executed based on the individual differences stored in the storage.

Accordingly, the orientation can be measured accurately.

In the orientation meter, the signal from the light receiving element is loaded by using a reference position signal and a timing signal for making the plurality of light emitting elements sequentially emit light, or by using the reference position signal and a signal from a circuit that catches the sequentially emitted light as a timing signal.

Accordingly, accuracy of the measuring position can be maintained.

In the orientation meter, an order of emitting light of the plurality of light emitting elements makes a substantially uniform distribution.

Accordingly, the accurate measurement by online in which the measuring face changes over time can be carried out.

In the orientation meter, the light from the light emitting element for irradiating the measuring object is a P polarized light or a S polarized light.

Accordingly, S/N can be increased.

In the orientation meter, the light receiving element is a semiconductor photodetector, and the light emitting element is a light emitting diode (LED) or a laser diode.

Accordingly, the orientation meter can be downsized.

In the orientation meter, at least one timing signal for making the plurality of light emitting elements sequentially emit light or at least one signal from a circuit that catches the sequentially emitted light as a timing signal is used as a reference position signal by changing a duty of at least one timing signal or at least one signal from the circuit with other signal, and the signal from the light receiving element is loaded by using the reference position signal.

Accordingly, the light emitting timing and the reference position signal can be put together as one signal and therefore, a reduction in cost and downsizing of the orientation meter can be achieved.

In the orientation meter, a frequency of the light emitted from the respective light emitting elements is changed in accordance with a characteristic of the measuring object.

Accordingly, the highly accurate measurement an be carried out in accordance with the characteristic of the measuring object.

In the orientation meter, a number of the plurality of light emitting elements is even, the plurality of light emitting elements is arranged along a circumference, and two of the light emitting elements that are opposed to each other emit light simultaneously.

Accordingly, even when the surface of the measuring object is wavy, the averaged output can be achieved. Further, since the light amount is increased, S/N can be increased and a sweep time period can be halved.

The orientation meter further including:

a software for calculating an orientation direction of the measuring object having a fiber orientation and an orientation direction of the measuring object having a molecular orientation, wherein the software is switched to calculate the orientation direction of the measuring object having the fiber orientation or the orientation direction of the measuring object having the molecular orientation in accordance with a usage.

Accordingly, two kinds of the measuring objects can be measured by the same component.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An orientation meter for measuring an orientation of a measuring object, the orientation meter comprising:
   a plurality of light emitting elements for irradiating light to the measuring object;
   a light receiving element for receiving reflected light being reflected by the measuring object; and
   a gain adjusting light emitting element arranged at a vicinity of the light receiving element,
   wherein the plurality of light emitting elements is arranged around the light receiving element, and
   the orientation of the measuring object is measured based on a signal from the light receiving element.

2. The orientation meter according to claim 1, further comprising:
   the orientation meter
   a non-oriented reflector arranged at a position that is opposed to the light receiving element, the position being on a back face side of the measuring object.

3. The orientation meter according to claim 1, wherein the plurality of light emitting elements are arranged along a circumference at equal intervals by a predetermined angle with respect to a surface of the measuring object, and
   the light receiving element is arranged at the vicinity of a center of the light emitting elements.

4. The orientation meter according to claim 2, wherein the plurality of light emitting elements are arranged along a circumference at equal intervals by a predetermined angle with respect to a surface of the measuring object, and
   the light receiving element is arranged at the vicinity of a center of the light emitting elements.

5. The orientation meter according to claim 1, further comprising:
   a storage for storing individual differences of the respective light emitting elements,
   wherein in calculating an orientation direction of the measuring object, calibration is executed based on the individual differences stored in the storage.

6. The orientation meter according to claim 1, wherein the signal from the light receiving element is loaded by using a reference position signal and a timing signal for making the plurality of light emitting elements sequentially emit light, or by using the reference position signal and a signal from a circuit that catches the sequentially emitted light as a timing signal.

7. The orientation meter according to claim 3, wherein an order of emitting light of the plurality of light emitting elements makes a substantially uniform distribution.

8. The orientation meter according claim 1, wherein the light from the light emitting element for irradiating the measuring object is a P polarized light or a S polarized light.

9. The orientation meter according to claim 1, wherein the light receiving element is a semiconductor photodetector, and
   the light emitting element is a light emitting diode (LED) or a laser diode.

10. The orientation meter according to claim 1, wherein at least one timing signal for making the plurality of light emitting elements sequentially emit light or at least one signal from a circuit that catches the sequentially emitted light as a timing signal is used as a reference position signal by changing a duty of said at least one timing signal or said at least one signal from the circuit with other signal, and
    the signal from the light receiving element is loaded by using the reference position signal.

11. The orientation meter according to claim 1, wherein a frequency of the light emitted from the respective light emitting elements is changed in accordance with a characteristic of the measuring object.

12. The orientation meter according to claim 1, wherein a number of the plurality of light emitting elements is even,
    the plurality of light emitting elements is arranged along a circumference, and
    two of the light emitting elements that are opposed to each other emit light simultaneously.

13. The orientation meter according to claim 1, further comprising:
    a software for calculating an orientation direction of the measuring object having a fiber orientation and an orientation direction of the measuring object having a molecular orientation,
    wherein the software is switched to calculate the orientation direction of the measuring object having the fiber orientation or the orientation direction of the measuring object having the molecular orientation in accordance with a usage.

* * * * *